United States Patent
Minato

[19]

[11] Patent Number: 6,135,597
[45] Date of Patent: Oct. 24, 2000

[54] ARTIFICIAL VISION LENS SYSTEM AS WELL AS ARTIFICIAL VISION CAMERA AND ARTIFICIAL VISION SYSTEM USING THE SAME

[75] Inventor: Atsuo Minato, Tokyo, Japan

[73] Assignee: Hoya Corporation, Tokyo, Japan

[21] Appl. No.: 09/258,139

[22] Filed: Feb. 26, 1999

[30]  Foreign Application Priority Data

Mar. 6, 1998  [JP]  Japan .................................. 10-055404

[51] Int. Cl.[7] ...................................................... A61B 3/10
[52] U.S. Cl. ............................................ 351/216; 623/4.1
[58] Field of Search .................................... 351/205, 216, 351/217, 218, 219, 221, 237, 246, 247, 176; 250/227.2; 382/258, 266; 623/4.1; 359/487, 488, 494, 497, 498, 499

[56]  References Cited

U.S. PATENT DOCUMENTS 4,437,734  3/1984  Iizuka ........................ 359/487
5,532,770  7/1996  Schneider et al. ................ 351/205
5,546,142  8/1996  Kobayashi ........................ 351/237

FOREIGN PATENT DOCUMENTS

0 734 683 A2  10/1996  European Pat. Off. .

*Primary Examiner*—George Manuel
*Attorney, Agent, or Firm*—Griffin & Szipl, P.C.

[57]  ABSTRACT

An artificial vision lens system suitable for simulating a retinal image obtained when a subject wears eyeglass lenses. The artificial vision lens system 3 corresponding to an ocular optical system is designed based on optical constants of a paraxial area calculated from a Glustrand's precision simulated eye. The artificial vision lens system 3 comprises, in order from the object side, a front lens group 31 composed of lenses $L_1$ and $L_2$ and having negative refracting power, a stop 32, and rear lens group 33 composed of lenses $L_3$ through $L_6$ and having positive refracting power. Positions of the object side principal point and the turning point of the artificial vision lens system 3 may be set at positions suitable for simulating the eyeglass lens and the eyeball. An image (retinal image) of the artificial vision lens system 3 is imaged by a CCD 5.

20 Claims, 12 Drawing Sheets

| | RADIUS OF CURVATURE (mm) | GAP BETWEEN FACES (mm) | REFRACTIVE INDEX | ABBE'S NUMBER |
|---|---|---|---|---|
| L1 | $r_1$ = -7.05 | $r_1 \sim r_2$ = 1.00 | $n_1$ = 1.80610 | $\nu_1$ = 33.3 |
| | $r_2$ = -13.41 | | | |
| L2 | $r_3$ = -8.43 | $r_2 \sim r_3$ = 2.40 | $n_2$ = 1.51680 | $\nu_2$ = 64.4 |
| STOP | $r_4$ = ∞ | $r_3 \sim r_4$ = 1.50 | | |
| L3 | $r_5$ = 39.73 | $r_4 \sim r_5$ = 1.95 | $n_3$ = 1.56384 | $\nu_3$ = 60.8 |
| | $r_6$ = -23.46 | $r_5 \sim r_6$ = 2.14 | | |
| L4 | $r_7$ = 11.53 | $r_6 \sim r_7$ = 0.20 | $n_4$ = 1.58913 | $\nu_4$ = 61.2 |
| | $r_8$ = -154.30 | $r_7 \sim r_8$ = 4.71 | | |
| L5 | $r_9$ = 9.56 | $r_8 \sim r_9$ = 0.20 | $n_5$ = 1.71300 | $\nu_5$ = 54.1 |
| | $r_{10}$ = 34.68 | $r_9 \sim r_{10}$ = 2.00 | | |
| L6 | $r_{11}$ = -108.00 | $r_{10} \sim r_{11}$ = 0.20 | $n_6$ = 1.80610 | $\nu_6$ = 33.3 |
| | $r_{12}$ = 5.71 | $r_{11} \sim r_{12}$ = 1.00 | | |

FIG.8

| OPTICAL SYSTEM / OPTICAL CONSTANTS | ARTIFICAL VISION LENS | | GLUSTRAND'S SIMULATED EYE (D-LINE) |
|---|---|---|---|
| | E-LINE | D-LINE | |
| FOCAL LENGTH | 17.039mm | 17.052mm | 17.053mm |
| REFRACTING POWER | 58.69D | 58.64D | 58.64D |
| BACK FOCUS | 10.98mm | 10.99mm | |
| F NUMBER | 2.54 | 2.54 | |
| OBJECT SIDE PRINCIPAL POINT | 1.325mm | 1.350mm | 1.348mm |
| IMAGE SIDE PRINCIPAL POINT | -7.057mm | -7.060mm | |
| POSITION OF PUPIL ENTRANCE | 2.753mm | 2.759mm | 3.047mm |
| POSITION OF PUPIL EXIT | -5.739mm | -5.759mm | |

ARTIFICIAL VISION LENS SYSTEM AS WELL AS ARTIFICIAL VISION CAMERA AND ARTIFICIAL VISION SYSTEM USING THE SAME

FIELD OF THE INVENTION

The present invention relates to an artificial vision lens system as well as an artificial vision camera and an artificial vision system using the same which are suitable for observing how things are seen when a subject wears eyeglasses. The invention also relates to a method for simulating the optics of an eyeball.

BACKGROUND OF THE INVENTION

Because an ocular optical system is very complicated and it is very difficult to handle as it is, various simulated eyes have been considered as a standard optical model of an eyeball. In addition, studies of the optical characteristics of an eyeball (e.g., changes of various optical images when an intraocular lens is implanted) have been conducted by using such simulated eyes or by computer simulation using optical constants calculated from such simulated eyes.

Various lenses such as a progressive multi-focus lens are presently being developed in the field of eyeglass lenses. However, it has heretofore not been possible to objectively observe how things are seen when a subject wears an eyeglass lens. This difficulty has been a big obstacle in the research and development of eyeglass lenses.

Although it is conceivable to use an optical system corresponding to an eyeball to actually simulate an image (retinal image) of an object when seen through an eyeglass lens, the following problems have presented themselves when a ready made industrial lens, a photographing lens or the like are used in such a simulation.

Figure 14:
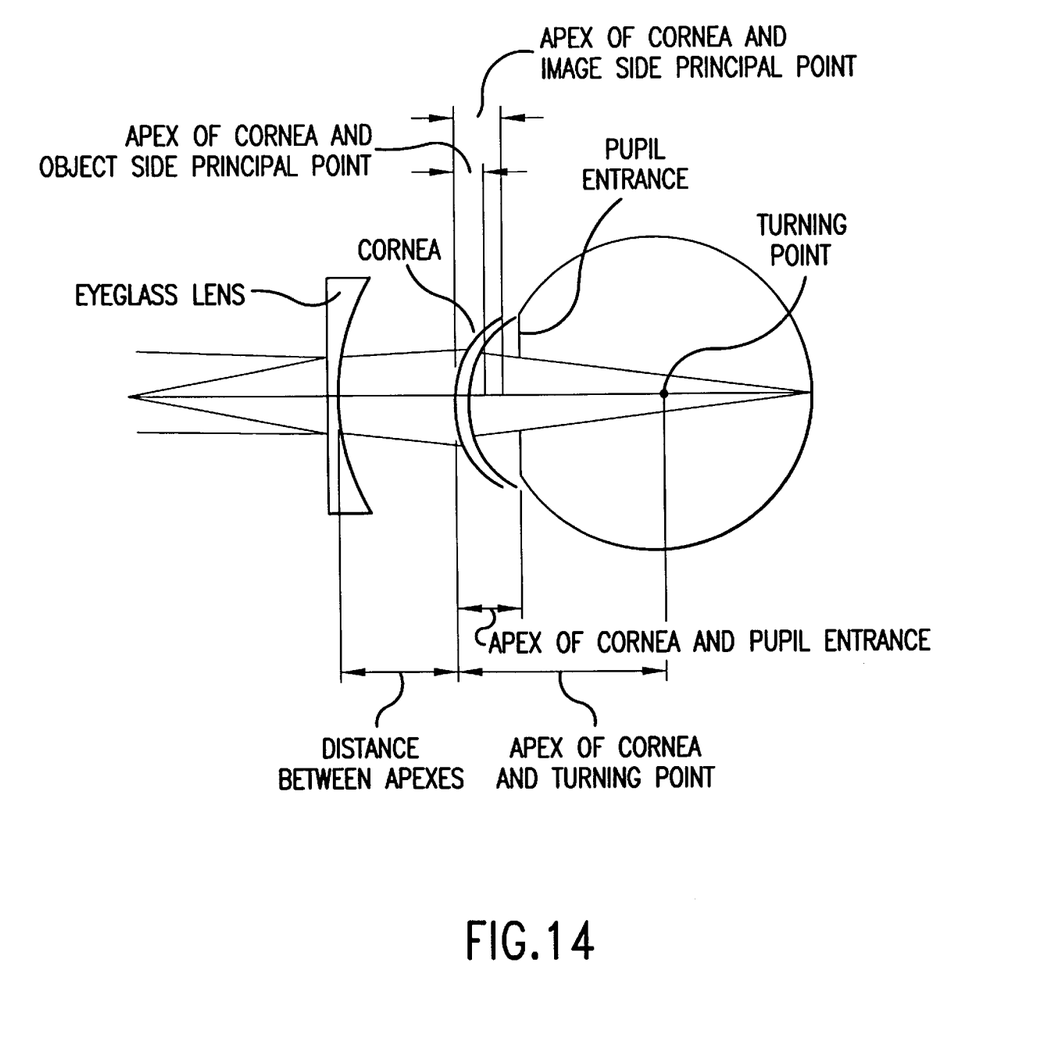
FIG. 14 is an explanatory diagram for explaining the formation of an image formed by the eyeglass lens and a simulated eye that replaces an eyeball according to the present invention.

When an optical system replacing an eyeball as shown in FIG. 14 is used, while light which is transmitted through an eyeglass lens advances toward a pupil of an eye (pupil entrance), brightness of an image and the size of a field of view change when a distance between the apexes of the rear faces of the eyeglass lens, the retina and the position of the pupil (position of the pupil entrance) shift. Therefore, it is necessary to give due consideration to the above-mentioned distance and the position so that they can be set correctly. However, the eyeglass lens and the state of the eyeball cannot be simulated by ready-made photographic and industrial lenses because the position of their object side principal point and that of the pupil entrance are located on the rear side as compared to the eyeball, and the distance between the apexes cannot be set correctly. That is, because the brightness of the image and the size of the field of view largely change in simulating the retinal image by using an eyeglass lens and an optical system such as ready-made photographing lenses, the eyeglass lens cannot be evaluated correctly.

Accordingly, it is an object of the present invention to provide an artificial vision lens system as well as an artificial vision camera and an artificial vision system suitable for simulating a retinal image of naked eyes or an image created when a subject wears eyeglass lenses.

SUMMARY OF THE INVENTION

In order to achieve the above-mentioned object, an artificial vision lens system is provided according to the present invention corresponding to an optical system of an eyeball and designed based on optical constants of a paraxial area calculated from a simulated eye.

While only a narrow retinal image at the fovea part is clearly perceived by human eyes, the image in this narrow field of view may be simulated and optical characteristics of the human eye in the paraxial area may be fully approximated by designing an artificial vision lens system based on a simulated eye (such as Glustrand's precision simulated eye) whose optical constants (focal length, position of pupil entrance, etc.) in the paraxial area are not significantly different from those of the human eye. Further, the artificial vision lens system may be relatively easily manufactured. The use of the artificial vision lens system according to the present invention allows a retinal image of naked eyes to be simulated.

The artificial vision lens system of the present invention corresponding to an optical system of an eyeball is also designed based on optical constants of a paraxial area calculated from a simulated eye so as to be able to simulate the positional relationship between an eyeglass lens and an object side principal point of an eyeball.

The use of the artificial vision lens system according to the present invention allows the position of the eyeglass lens and that of a pupil entrance of the artificial vision lens system to be set correctly with respect to the position of the object side principal point of the artificial vision lens system in accordance to the positional relationship between the eyeglass lens, and allows the eyeball and the retinal image to be simulated accurately.

Preferably, the artificial vision lens system according to the present invention comprises, in order from an object side, a front lens group having negative refracting power, a stop, and rear lens group having positive refracting power, wherein the system is arranged such that the focal position can be controlled by moving the rear lens group. By constructing the system as described above, the focal position may be controlled without changing the position of the pupil entrance of the artificial vision lens system.

In a still further embodiment of the present invention, the inventive artificial vision camera comprises the above-mentioned artificial vision lens system and a planar image-pickup for picking up an image formed by the artificial vision lens system. The planar image-pickup corresponds to the retinal image. This artificial vision camera allows the retinal image obtained when a subject wears an eyeglass lens to be simulated.

Characteristics equivalent to the human vision, etc., are preferably realized and the artificial vision camera is compactly constructed by using CCDs as the planar image-pickup in the above-mentioned artificial vision camera.

A still further embodiment of the present invention provides an inventive artificial vision system comprising the above-mentioned artificial vision camera and display means for displaying the image picked up by the artificial vision camera. The use of this artificial vision system allows the retinal image obtained when a subject wears an eyeglass lens to be observed in real-time.

Another embodiment provides an artificial vision lens system for simulating an optical system of an eyeball, comprising an artificial vision camera having an arrangement of lenses having optical constants of a paraxial area calculated from a simulated eye.

In accordance with a still further embodiment of the present invention there is provided an artificial vision lens system for simulating an optical system of an eyeball, comprising an artificial vision camera having optical constants of a paraxial area calculated from a simulated eye, preferably a Glustrand's precision simulated eye, and a holder configured to hold an eyeglass lens, the holder being arranged to simulate the relative positions between an eyeglass lens and an object side principal point of an eyeball when a subject wears an eyeglass lens. The artificial vision camera preferably has an object side and further comprises, arranged sequentially from the object side of the camera, a front lens group having negative refracting power, a stop, and rear lens group having positive refracting power, wherein a focal position of the camera is controllable by moving the rear lens group. The camera also preferably comprises a planar image-pickup arranged to pickup an image picked up by the camera, and a display operably connected to display an image picked up by the artificial vision camera.

In accordance with a yet further embodiment of the present invention, there is provided a method for simulating optics of an eyeball. The method preferably comprises the steps of: providing an artificial vision camera having optical constants of a paraxial area calculated from a simulated eye; and disposing an eyeglass lens relative to the artificial vision camera in a position simulating the relative position of an eyeglass lens and an object side principal point of an eyeball of a subject wearing the eyeglass lens. The simulated eye is preferably a Glustrand's precision simulated eye. The artificial vision camera preferably has an object side and comprises, arranged sequentially from the object side of the camera, a front lens group having negative refracting power, a stop, and rear lens group having positive refracting power, wherein a focal position of the camera is controllable by moving the rear lens group. The camera also preferably comprises a planar image-pickup arranged to pickup an image picked up by the camera, and a display for displaying the image.

Further objects, features and advantages of the present invention will become apparent from the Detailed Description of the Preferred embodiments, which follows, when considered together with the attached figures of drawing.

BRIEF DESCRIPTION OF DRAWINGS

FIGS. 10-1(a) through 10-3(c) are diagrams for explaining rotary and parallel movements of the artificial vision camera and the eyeglass lens to simulate the positional relationship between an eyeball, the eyeglass lens and the standard measuring object when the eyeball is turned.

DETAILED DESCRIPTION OF THE PREFERRED EMBODIMENTS

Modes for carrying out the invention will be explained below in detail by reference to the drawings, in which like parts are represented by like reference numerals.

Figure 1:
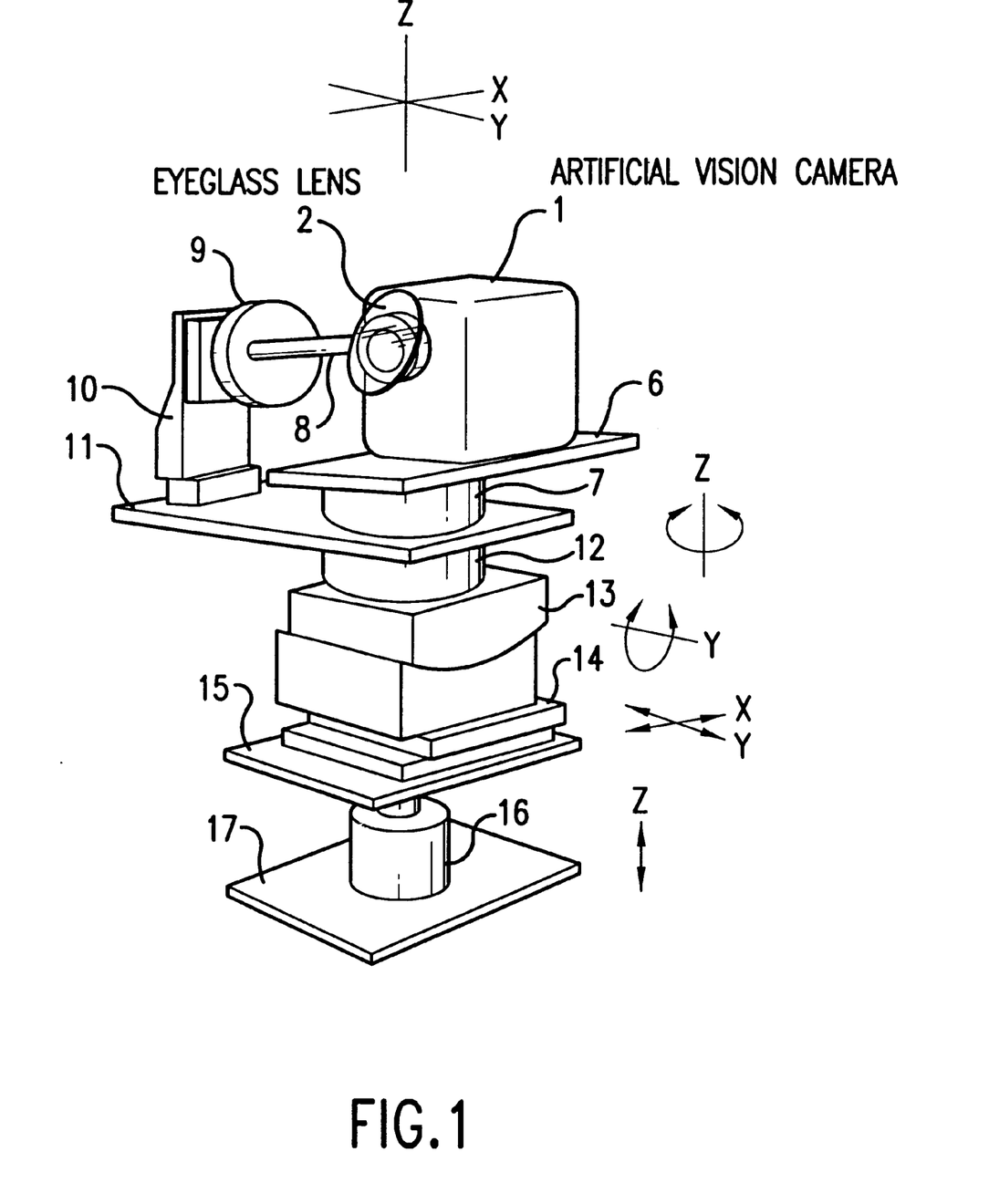
FIG. 1 is a perspective view showing one embodiment of an artificial vision system according to the present invention.
Figure 2A:
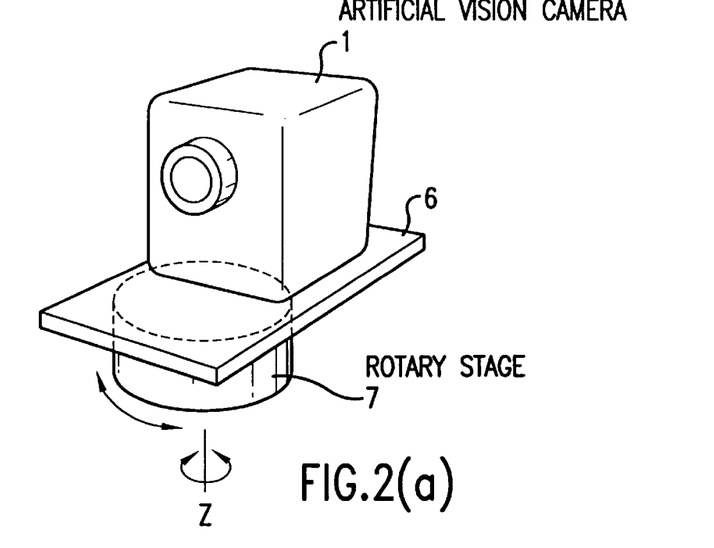
FIGS. 2a through 2c are explanatory diagrams for explaining the turning of the artificial vision camera and lens shown in FIG. 1.
Figure 2B:
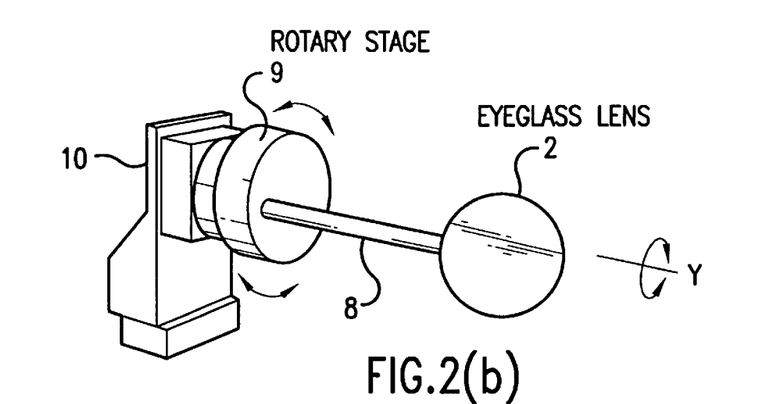

FIG. 1 is a perspective view of one embodiment of an artificial vision system according to the present invention. In FIG. 1, the reference numeral (1) denotes an artificial vision camera. An artificial vision lens system corresponding to an ocular optical system and a CCD camera having CCDs as a planar image-pickup corresponding to a retina are provided within the artificial vision camera 1. An eyeglass lens 2 is provided in front of the artificial vision camera 1 so as to face an artificial vision lens system 3 as shown in FIGS. 1 through 3.

Figure 5A:
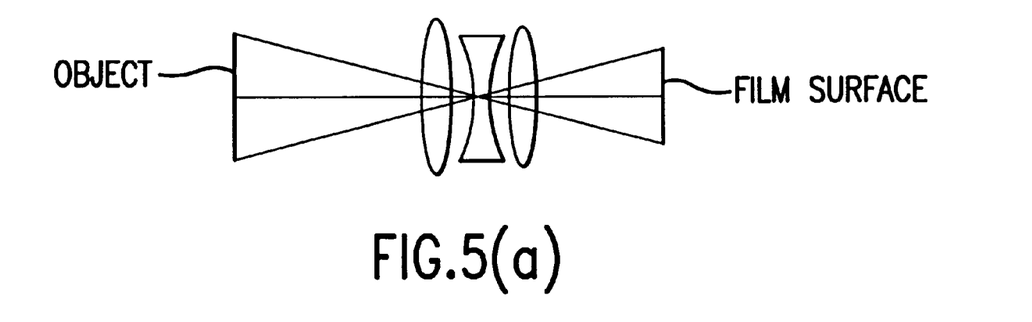
FIGS. 5a and 5b are explanatory diagrams for explaining a difference between an ordinary optical system and an eyeglass optical system.
Figure 5B:
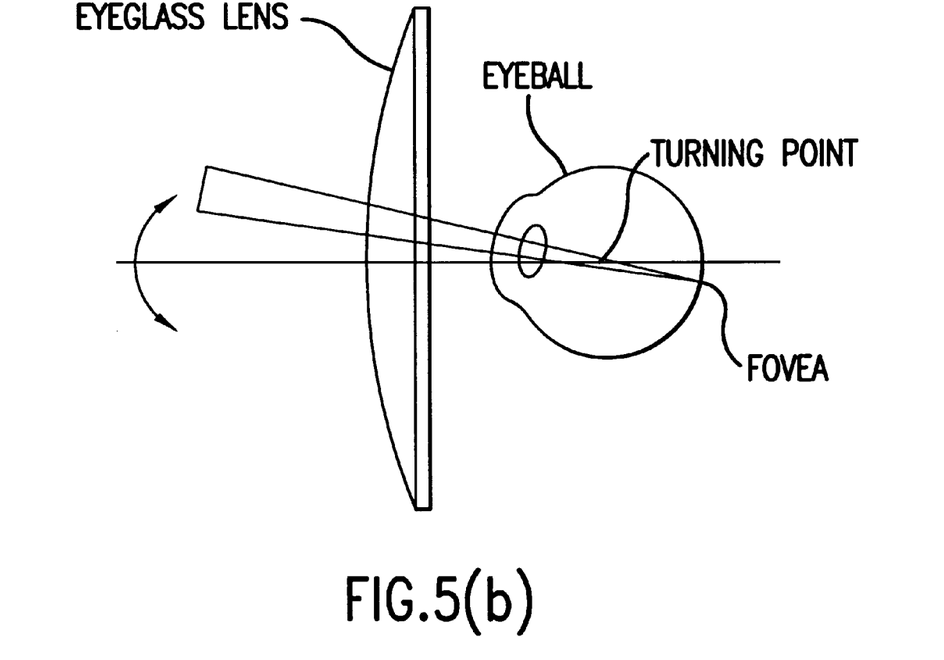

It is necessary to consider differences between ordinary optical systems (cameras, telescopes and the like) in simulating an eyeglass lens and an eyeball. Specifically, although an object in a wide range can be imaged on a surface of a film at a time in the case of an ordinary optical system, e.g., a camera, as shown in FIG. 5a, the eyeball receives an image in a wide range while turning centering on its turning point as shown in FIG. 5b. Thus, not all images imaged on the retina of the eye are perceived as clear images and only an image in a narrow area of the fovea part with high resolution is seen as a clear image. Accordingly, it is necessary to take the rotary movement (ocular movement) centering on the turning point of the eyeball into consideration in simulating the eyeglass lens and the eyeball as a single optical system. This requires a system and an arrangement which allows an optical axis (or a visual line) and an image surface to be always constantly evaluated and the position of the eyeglass lens where light flux passes through to be changed in accordance with the turning of the eyeball to obtain the same effect as the rotary movement of the eyeball centering on the turning point with respect to the eyeglass lens.

Figure 2C:
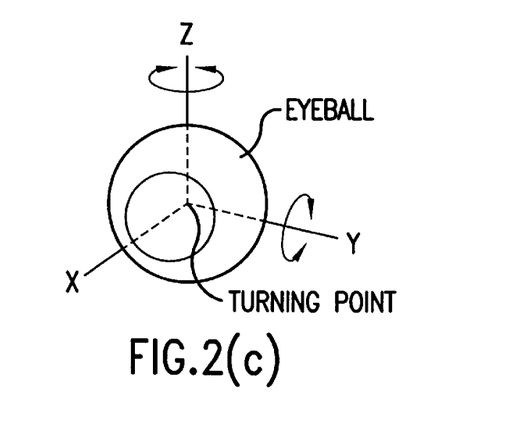
Figure 3:
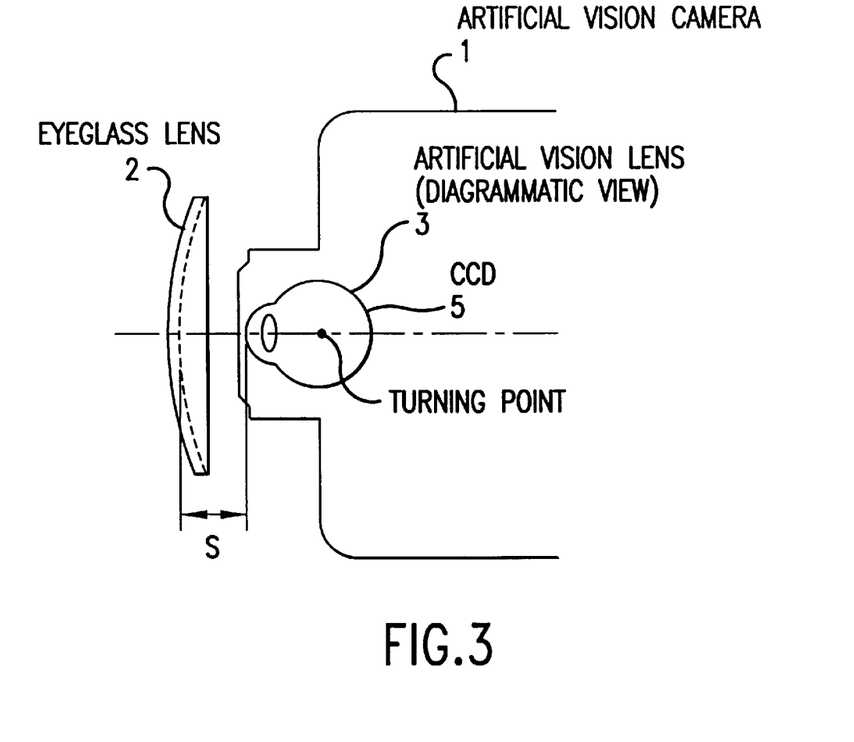
FIG. 3 is a diagram showing the positional relationship between the eyeglass lens and an artificial vision lens system within the artificial vision camera.
Figures 3A, 10:
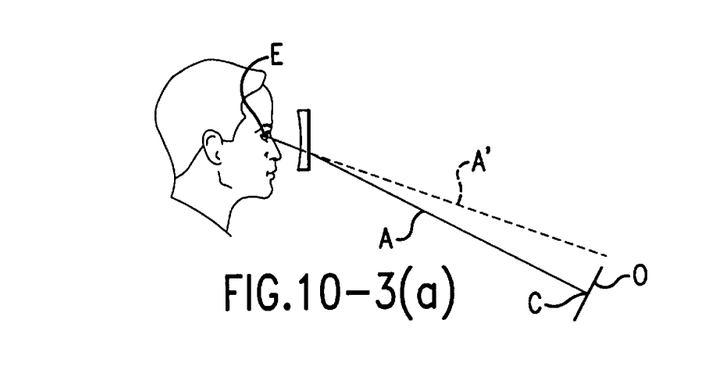
Figures 3B, 10:
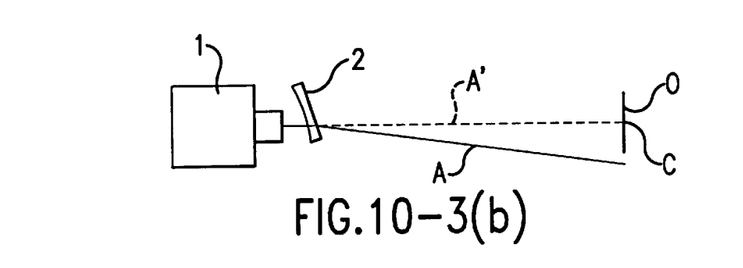
Figures 3C, 10:
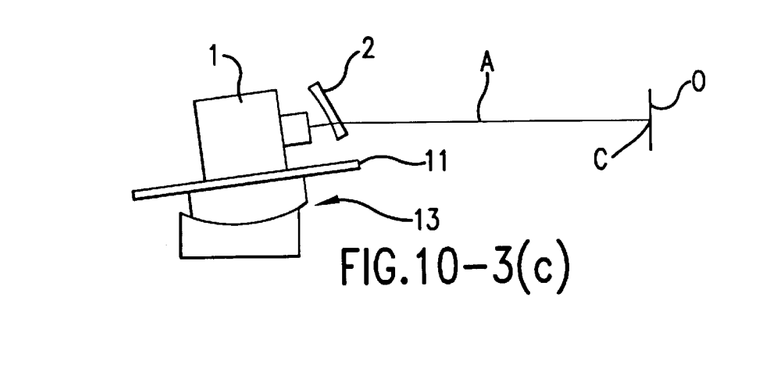

The rotary movement (ocular movement) of the eyeball around the turning point may be realized by combining rotation in the horizontal direction (rotation around a Z-axis passing through the turning point of the eyeball) and rotation in the vertical direction (rotation around a Y-axis passing through the turning point of the eyeball) as shown in FIG. 2c. According to the present embodiment, the rotary movement of the eyeball is arranged such that the rotation in the horizontal direction (rotation around a Z-axis passing through a turning point of the artificial vision lens system) is imparted to the artificial vision camera 1 and rotation in the vertical direction (rotation around a Y-axis passing through the turning point of the artificial vision lens system) is imparted to the eyeglass lens 2.

That is, the rotation in the horizontal direction (right and left direction) is made possible by placing the artificial vision camera (artificial vision lens system and CCD camera) 1 on a mount 6 on a rotary stage 7 as shown in FIGS. 1 and 2a. Furthermore, the artificial vision camera 1 is arranged such that its position can be adjusted with the center of rotation of the rotary stage 7 so that the position of the center of rotation of the rotary stage 7 coincides with the position of the turning point of the artificial vision lens system. This arrangement allows the same effect to be obtained as the rotary movement of the eyeball in the horizontal direction centering on the turning point.

The eyeglass lens 2 is attached to a rotary stage 9 via a supporting rod 8 as shown in FIGS. 1 and 2b so that the eyeglass lens 2 can be turned in the vertical direction (up and down direction) by turning the rotary stage 9. Lens 2 is also arranged such that a distance S from the rear face of the eyeglass lens 2 to the first face (corresponding to the apex of a cornea of an eyeball) of the artificial vision lens system 3 may be adjusted as shown in FIG. 3, so that the position of the center of rotation of the rotary stage 9 preferably coincides with the position of the turning point of the artificial vision lens system 3. Thereby, the same effect as rotary movement of the eyeball in the vertical direction centering on the turning point is obtained.

Figure 4:
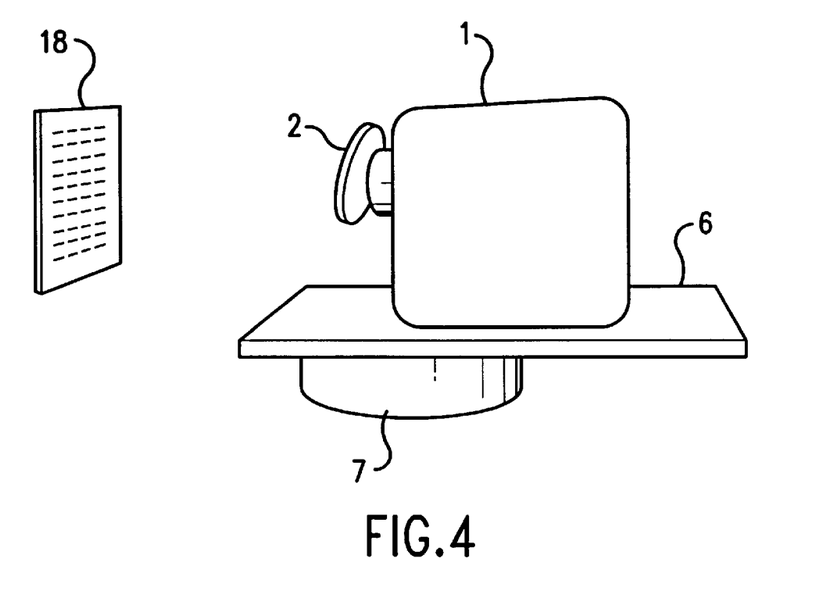
FIG. 4 is a perspective view showing a state in which the artificial vision camera views a standard measuring object through a near-sighted section of an eyeglass lens.

The same effect as rotary movement (ocular movement) of the eyeball centering on the turning point is obtained by appropriately combining these two rotary movements in the horizontal and vertical directions. FIG. 4 shows, for example, a state in which the artificial vision camera 1 views a nearby standard measuring object 18. such as a newspaper, for example, through a near-sighted section of the eyeglass lens (multi-focus lens) 2.

The rotary stage 7 for turning the artificial vision camera 1 and a supporting section 10 for supporting the rotary stage 9 for turning the eyeglass lens 2 are provided on a stage 11. The eyeglass lens 2 and the artificial vision camera 1 are arranged so as to be able to turn by about 30 degrees respectively in the up and down and right and left directions.

In this way, in order to evaluate the performance of the eyeglass lens 2 with a standard measuring object (e.g., chart) it is necessary to observe a retinal image at each point where the position of light flux from an object (e.g., chart) on the outside transmited through the eyeglass lens 2 changes along with the turning of the eyeball. It is very difficult to realize this objective because a large number of charts have to be set within a three-dimensional space (in a wide area in a wide range in up and down and right and left directions and from the nearby to the distant) which is visible by changing a line of sight when the artificial vision camera corresponding to an eyeball is turned up and down and to the right and left around the turning point.

The chart (standard measuring object) is thus fixed in one direction and three-dimensional turning and parallel movement are applied to the artificial vision camera 1 and the eyeglass lens 2 to simulate the positional relationship among the eyeball, the eyeglass lens and the chart when the eyeball turns in the present embodiment. That is, a turning and parallel movement mechanism is provided under the stage 11 on which the eyeglass lens 2 and the artificial vision camera 1 are mounted so that the optical axis (visual axis) of the artificial vision camera 1 always points toward the chart (standard measuring object) in a fixed direction while simulating the rotary movements of the eyeball centering on the turning point with respect to the eyeglass lens. This objective is achieved by turning the artificial vision camera 1 in the horizontal direction by means of rotary stage 7 and the turning the eyeglass lens 2 in the vertical direction by means of the rotary stage 9 as described above.

This aspect of the present invention will be further concretely explained by setting the direction of the optical axis (visual axis) of the artificial vision camera 1 as an X-direction, the direction of right and left with respect to the eyeglass lens 2 as a Y-direction and the direction of up and down with respect to the eyeglass lens 2 as a Z-direction, as shown in FIG. 1. Under the stage 11 on which the eyeglass lens 2 and the artificial vision camera 1 are mounted are: a rotary stage 12 turning around the Z-axis, a gonio-stage 13 turning around the Y-axis, an XY stage 14 moving in parallel in the X and Y directions and an a Z stage 16 moving in parallel in the Z-direction. The system is also arranged such that turning around the X-axis is achieved by processing an image taken into the artificial vision camera 1. (In FIG. 1, reference numeral 15 denotes a mounting plate of the XY stage 14 and 17 denotes a base board).

Thereby, the optical axis (visual axis) of the artificial vision camera 1 may be set so as to always point toward the chart (standard measuring object) at a fixed direction through eyeglass lens 2. That is, the positional relationship among the eyeball, the eyeglass lens and the standard measuring object when the eyeball is turned may be simulated, even with the measuring object at a fixed position, by applying three-dimensional rotary and linear movements to the artificial vision camera 1 and the eyeglass lens 2. This feature will now be explained more concretely below.

Figure 102:
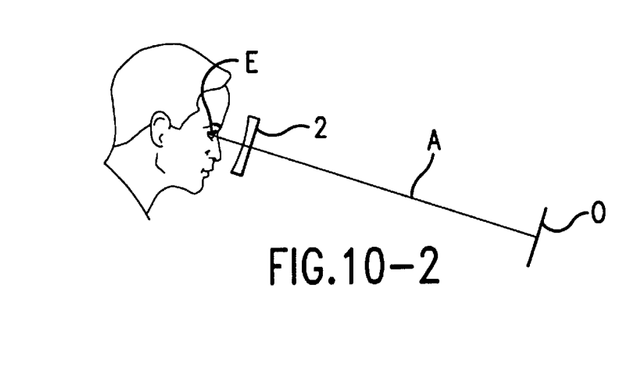

FIG. 10-1(a) shows a state in which a subject wearing an eyeglass lens 2, such as, for example, a progressive multi-focus lens, is viewing a standard measuring object O through a far-sighted section of eyeglass lens 2 while keeping his posture straight and his line of sight horizontal. In this state, a visual axis (optical axis) A of an eyeball E is a straight line which advances linearly and passes through the eyeglass lens 2. The relationship among the eyeball E, the eyeglass lens 2 and the standard measuring object O at this time may be simulated by keeping a visual axis (optical axis) A of the artificial vision camera 1 horizontal as shown in FIG. 10-1(b) because the visual axis (optical axis) A advances linearly through the far-sighted section and faces the front of the measuring object O. FIG. 10-2 shows a case in which the subject tilts his neck (head) downward without moving the eyeball E from the state shown in FIG. 10-1(a), and the relationship among the eyeball E, the eyeglass lens 2 and the standard measuring object O is the same as that shown in FIG. 10-1(a). This case is also simulated as shown in FIG. 10-1(b).

However, when the subject views the standard measuring object O below him through the near-sighted section of the eyeglass lens 2 by moving only the eyeball E as shown in FIG. 10-3(a), the visual axis (optical axis) A of the eyeball E does not coincide with a straight line A' which advances linearly and extends through the eyeglass lens 2 as shown in FIG. 10-1(a). This is because the eyeglass lens 2 functions as a prism and the visual axis (optical axis) A is deflected by the eyeglass lens 2 and the eyeball E is views not in the A' direction, but in the A direction.

Accordingly, when only the eyeglass lens 2 is turned upward around the turning point of the artificial vision lens system as shown in FIG. 10-3(b), in order to simulate the downward turn of the eyeball E without changing the positional relationship between the artificial vision camera 1 and the measuring object O (while keeping the same state as that shown in FIG. 10-1(b), the visual axis A (shooting direction of the artificial vision camera 1) of the artificial vision camera 1 does not proceed linearly through the eyeglass lens 2 like the straight line A', but is rather deflected by the eyeglass lens 2 and does not point to the front of the fixed standard measuring object O. Thus, the performance of the eyeglass lens 2 cannot be evaluated correctly in such a case.

However, in order to solve this problem, the gonio-stage 13 under the stage 11 is turned while keeping the positional relationship (state shown in FIG. 10-3(b)) between the artificial vision camera 1 and the eyeglass lens 2 on the stage 11 as shown in FIG. 10-3(c) so that the visual axis (optical axis) A of the artificial vision camera 1 points to the front of standard measuring object O. Furthermore, the artificial vision camera 1 and the eyeglass lens 2 are moved up and down by the Z stage 16 under the stage 11 to adjust the system so that the visual axis (optical axis) A of the artificial vision camera 1 is positioned at the center point C of the standard measuring object O at each measuring position to simulate the case when the measuring object O is seen through the eyeglass lens 2 by turning the eyeball E.

Figures 1A, 1B, 10:
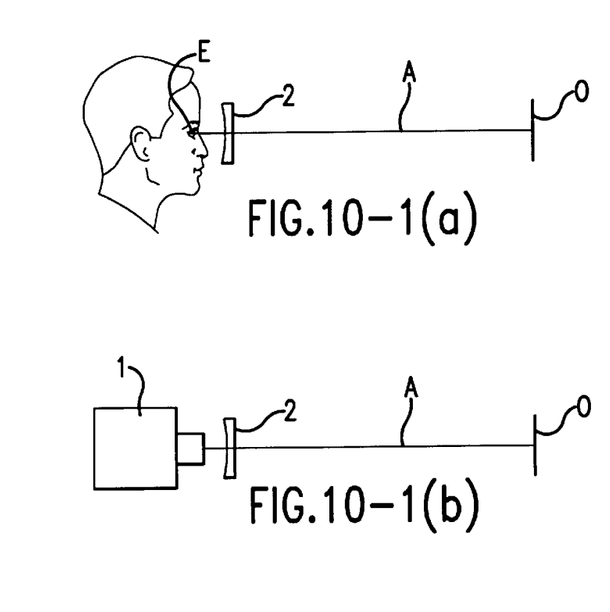

Although the method for correcting the deflection of the visual axis (optical axis) A of the artificial vision camera 1 has been explained for simplicity's sake only in the case of deflection in vertical direction caused by the eyeglass lens 2 when the eyeball E is turned as shown in FIG. 10. However, the visual axis (optical axis) A of the artificial vision camera 1 is actually deflected through the eyeglass lens 2 not only in the vertical direction but also in the horizontal direction when the eyeball E is turned in the vertical and horizontal directions.

Accordingly, the positional relationship between the eyeball E (and the eyeglass lens 2) and the standard measuring object O is realized by a three-dimensional turning and parallel movement mechanism (including image processing) such as rotary stage 12, gonio-stage 13, the XY stage 14 and Z stage 16 provided under stage 11. At the same time, the vertical turning of the eyeball E, simulated by the vertical turning of the eyeglass lens 2, and the horizontal turning of the eyeball E, simulated by the horizontal turning of the artificial vision camera 1, is carried out in order to simulate the positional relationship among the eyeball E, the eyeglass lens 2 and the measuring object O.

The structure under the stage 11 for simulating ocular movement by turning the artificial vision camera 1 and the eyeglass lens 2 may be realized by any suitable structure having a parallel movement and turning mechanism for movement in the direction of each of the X, Y and Z axes. For instance, it is possible to sequentially arrange a gonio-stage turning around the Y-axis right under the stage 11, and thereafter a rotary stage turning around the Z-axis, a Z stage moving in parallel to the Z direction and, lastly, an XY stage moving in parallel to the X and Y directions. Turning around the X-axis may be achieved by computer processing of images taken in.

The artificial vision lens system 3 will now be explained in detail.

While light which has passed through the eyeglass lens advances toward a pupil (pupil entrance) of the eye, brightness of an image and the size of the field of view change when a distance between the apexes of the rear face of the eyeglass lens and of the cornea and the position of the pupil (position of the pupil entrance) shift when the optical system replacing the eye as shown in FIG. 5 is used. Therefore, it is necessary to consider the abovementioned distance, so that the position can be correctly set. The artificial vision lens system 3 is designed and fabricated with reference to optical constants of a paraxial area calculated from a Glustrand's precision simulated eye, so that the positional relationship between the eyeglass lens and position of the object side principal point of the eyeball may be correctly simulated.

A number of simulated eyes whose ocular image-forming characteristics are adjusted to actual measurements have been proposed lately (e.g., one using an aspherical lens (R. Navarro, 1985), one in which a crystalline lens is multi-layered (O. Pomerantzeff, 1984) and one using a distributed index lens (J. Warren Blaker, 1980)). However, there have been technological problems in fabricating these simulated eyes. Therefore, the optical constants in the paraxial area of the Glustrand's precision simulated eye has been adopted in a preferred embodiment of the present invention because the optical constants (focal length, position of pupil entrance, etc.) of the human eye are not so different from those of the Glustrand's precision simulated eye in the paraxial area.

Figure 6:
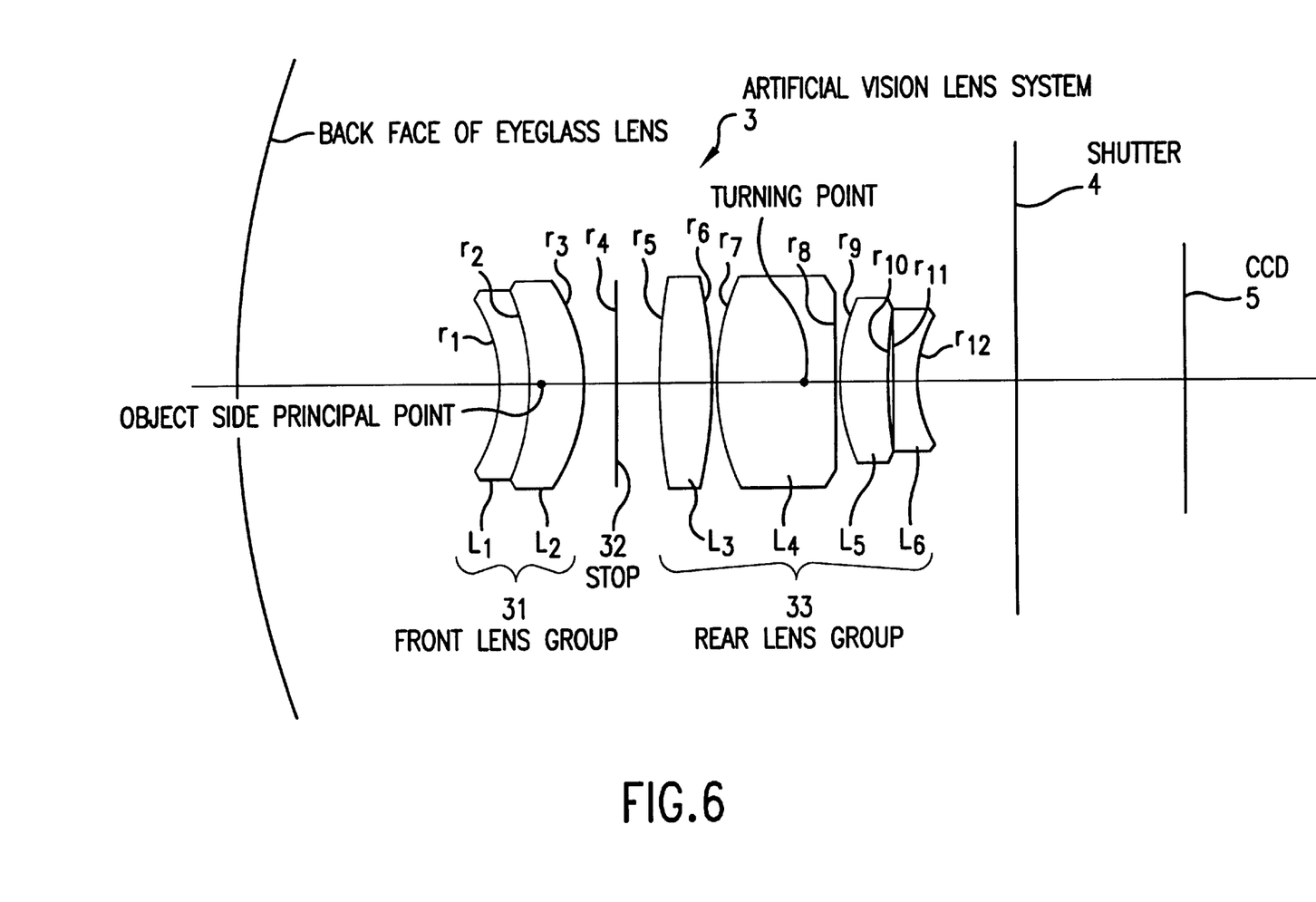
FIG. 6 is a diagram showing the arrangement of the artificial vision lens system according to the present invention, a shutter and CCDs of a CCD camera provided within the artificial vision camera.

FIG. 6 shows a preferred arrangement of the artificial vision lens system 3, a shutter 4 of the CCD camera and the CCDs (CCD surface) 5. As shown in FIG. 6, the artificial vision lens system 3 comprises, in order from the object side, a front lens group 31 composed of lenses $L_1$ and $L_2$ and having negative refracting power, a stop 32, and a rear lens group 33 composed of lenses $L_3$ through $L_6$ and having positive refracting power. The object side principal point of the whole system, the turning point, and the pupil entrance are disposed at positions suitable for simulating the eyeglass lens.

Figure 7A:
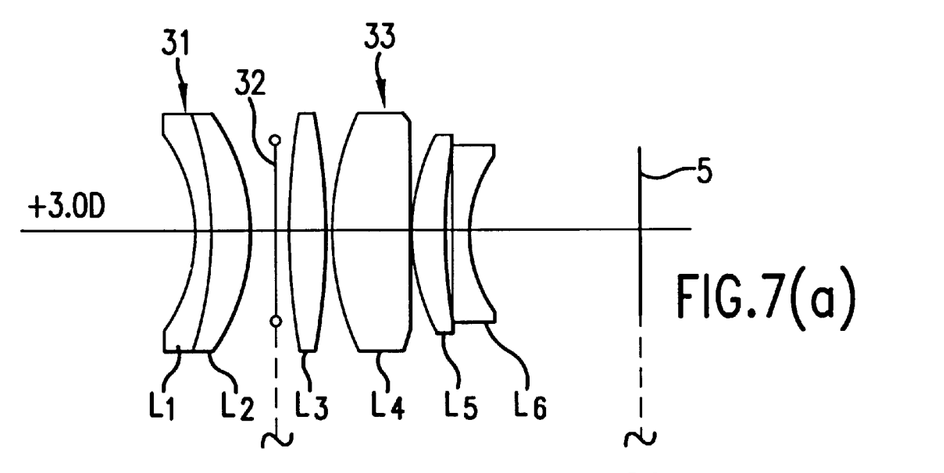
FIGS. 7a through 7c are diagrams for explaining accommodation of the focal position of the artificial vision lens system according to an embodiment of the present invention.
Figure 7B:
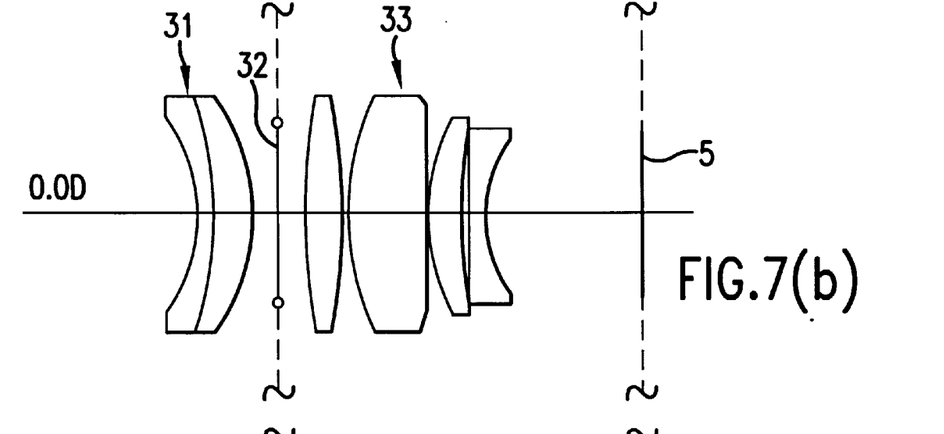
Figure 7C:
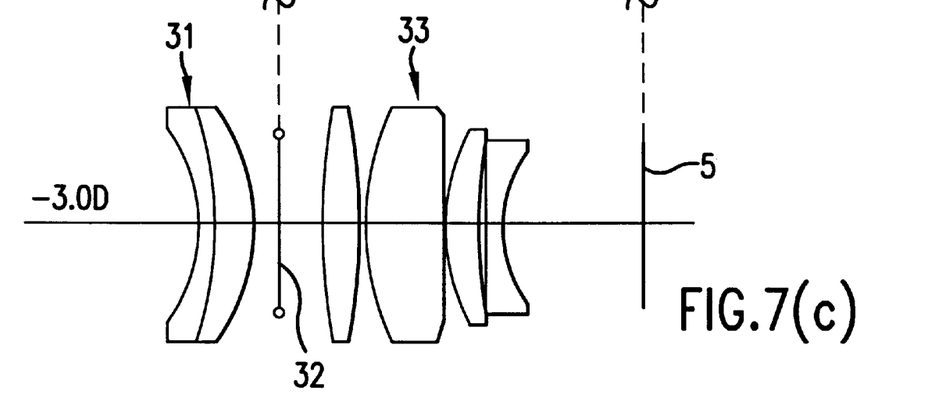

The focal position of the artificial vision lens system 3 may be accommodated with an accommodating ability of ±3.0 D (diopter) by moving the rear lens group 33 behind the stop 32 of the optical system as shown in FIG. 7. FIG. 7b shows the reference position at 0.0 D; FIG. 7a shows a state in which the rear lens group 33 is moved forward from the state in FIG. 7b to increase the refracting power by +3.0 D and FIG. 7c shows a state in which the rear lens group 33 is moved rearward from the state shown in FIG. 7b to reduce the refracting power by −3.0 D. Thus, the refracting power is controlled by moving the rear lens group 33 behind the stop 32, so that the position of the pupil entrance will not change even when the focal position of the artificial vision lens system 3 is changed. Furthermore, because the refracting power of the artificial vision lens system 3 may be changed, it is possible to simulate how things are seen corresponding to the accommodating ability of eyes of respective persons having normal vision, short-sightedness, far-sightedness, old-sighted eye, and the like.

Figure 8:
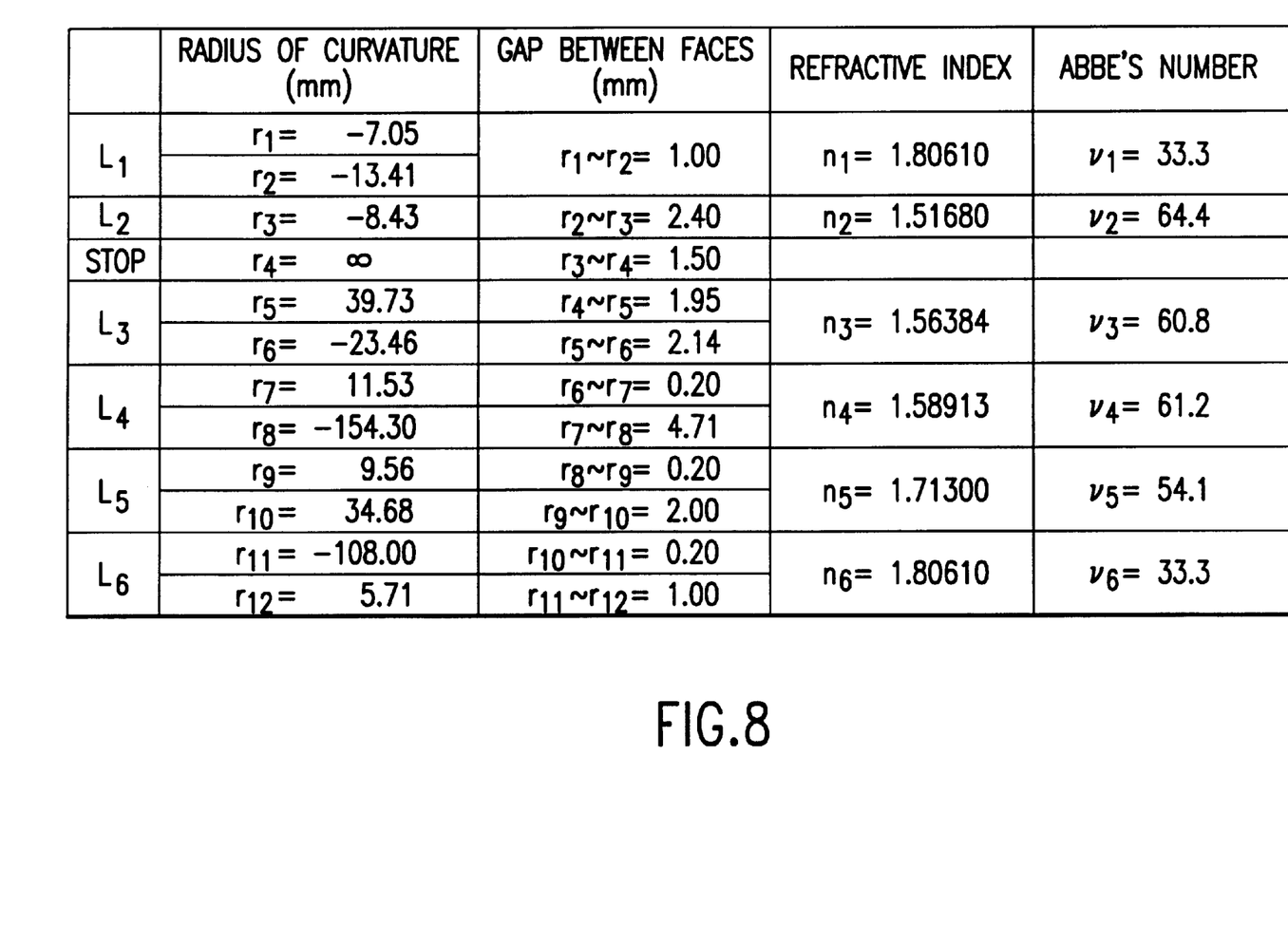
FIG. 8 is a table showing exemplary numerical data such as radius of curvature of each lens face of the artificial vision lens system according to the present invention.

FIG. 8 shows numerical data of the lenses $L_1$ through $L_6$. In FIG. 8, the respective symbols $r_1, r_2, \ldots$ denote a radius of curvature of each lens face (including the stop) (see FIG. 6) and $r_1$ to $r_2$, $r_3$ to $r_3$, ... denote gaps (distance on the optical axis) between the respective lens faces (including the stop). For example, $r_1$ to $r_2$ is a distance between the front face $r_1$ and the rear face $r_2$ of the lens $L_1$ (thickness of the lens $L_1$ on the optical axis). Further, $n_1, n_2, \ldots$ denote the refractive index of the respective lenses $L_1, L_2$ (on a d-line) and $v1, v2, \ldots$ denote the Abbe's number of the respective lenses $L_1, L_2, \ldots$ (on the d-line). In the exemplary embodiment, the front face of the lens $L_2$ and the rear face of the lens $L_1$ have the same radius of curvature $r_2$ and the lenses $L_1$ and $L_2$ are closely contacted. The gap $r_4$ to $r_5$ between the stop 32 and the front face of the lens $L_3$ changes when the rear lens group 33 is moved to change the accommodating ability of the above-mentioned 3. The value 1.95 mm of the gap $r_4$ to $r_5$ in FIG. 8 is the value in the case shown in FIG. 7b and the values of the gap $r_4$ to $r_5$ in case of FIGS. 7a and 7c are 0.95 mm and 2.95 mm, respectively. Furthermore, the stop 32 is preferably a fixed stop whose diameter is, for example, ϕ8.5 mm. However, the diameter of the stop may be changed to, for example, ϕ8.5, 6.0, 4.0 or 2.0 mm.

Figure 9:
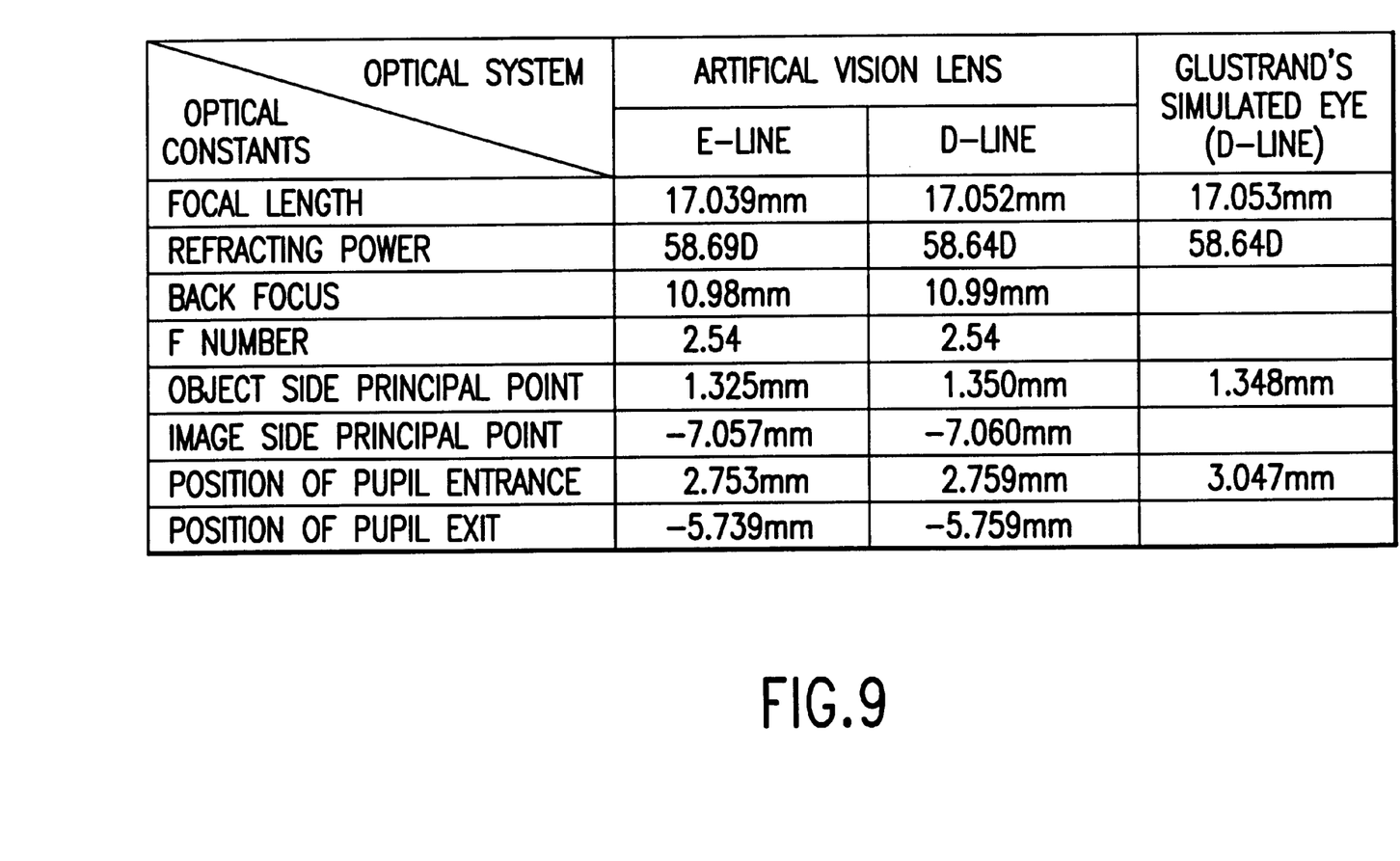
FIG. 9 is a table showing optical constants such as a focal length of an embodiment of the artificial vision lens system according to the present invention.

FIG. 9 shows the optical constants of the artificial vision lens system 3 designed as described above. Thereby, the eyeglass lens 2 may be disposed at an arbitrary position between 10 and 20 mm to the object side from the front face of the artificial vision lens system 3, and the turning point may be disposed at an arbitrary position between 10 to 22 mm to the image side from the front face of the artificial vision lens system 3.

Because the setting position may be controlled as described above, the positional relationship between the eyeglass lens, the object side principal point, and the turning point of the artificial vision lens system 3 in the artificial vision lens system 3 in FIG. 6 may be set in the same manner as the positional relationship between the eyeglass lens and the object side principal point and the turning point of the eyeball in FIG. 14. It should be noted that, in this embodiment, the position of the pupil entrance, not the position of the turning point, is set from the back face of the eyeglass lens or the object side principal point of the artificial vision lens system 3.

The part of the present system corresponding to a retina of a human eye is the CCD 5. Because the image surface is planar, the best image surface of the artificial vision lens system is arranged to be planar corresponding to the CCD surface. A high resolution CCD camera (Kodak Mega-plus 1.4 i) manufactured by Eastman Kodak Co. has been used as the CCD camera in the system according to the present invention. An effective photo-receiving area of the CCD 5 is 100% and its pixel size is 6.8 $\mu$m×6.8 $\mu$m. This corresponds to about 150 lines/mm in terms of spatial frequency and is equivalent to about 1.5 of visual acuity.

By reducing from 1.5 visual acuity, the MTF (Modulation Transfer Function) turns out to be 20 to 25% or more when the spatial frequency is 150 (lines/mm) in case of a human. It is known that the human eye presents a value more or less higher than the MTF of Glustrand's precision simulated eye because it includes not only the optical performances of the eyeball (retina, crystalline lens, etc.) but also the MTF of the retina, characteristics of the visual information processing mechanism in the neural network and the cerebrum, and the like (H Ohzu et, al., "Optical Modulation by the Isolated Human Fovea", Vision Res 12, 231 to 251 (1972)). Taking the above into account, the artificial vision lens system according to the present invention is preferably designed by setting the high-frequency side at a slightly higher value. When it is confirmed that the artificial vision lens system thus designed has been fabricated accurately, the relative evaluation and observation of an eyeglass lens may be favorably performed without being much influenced by the artificial vision lens system.

Figure 11:
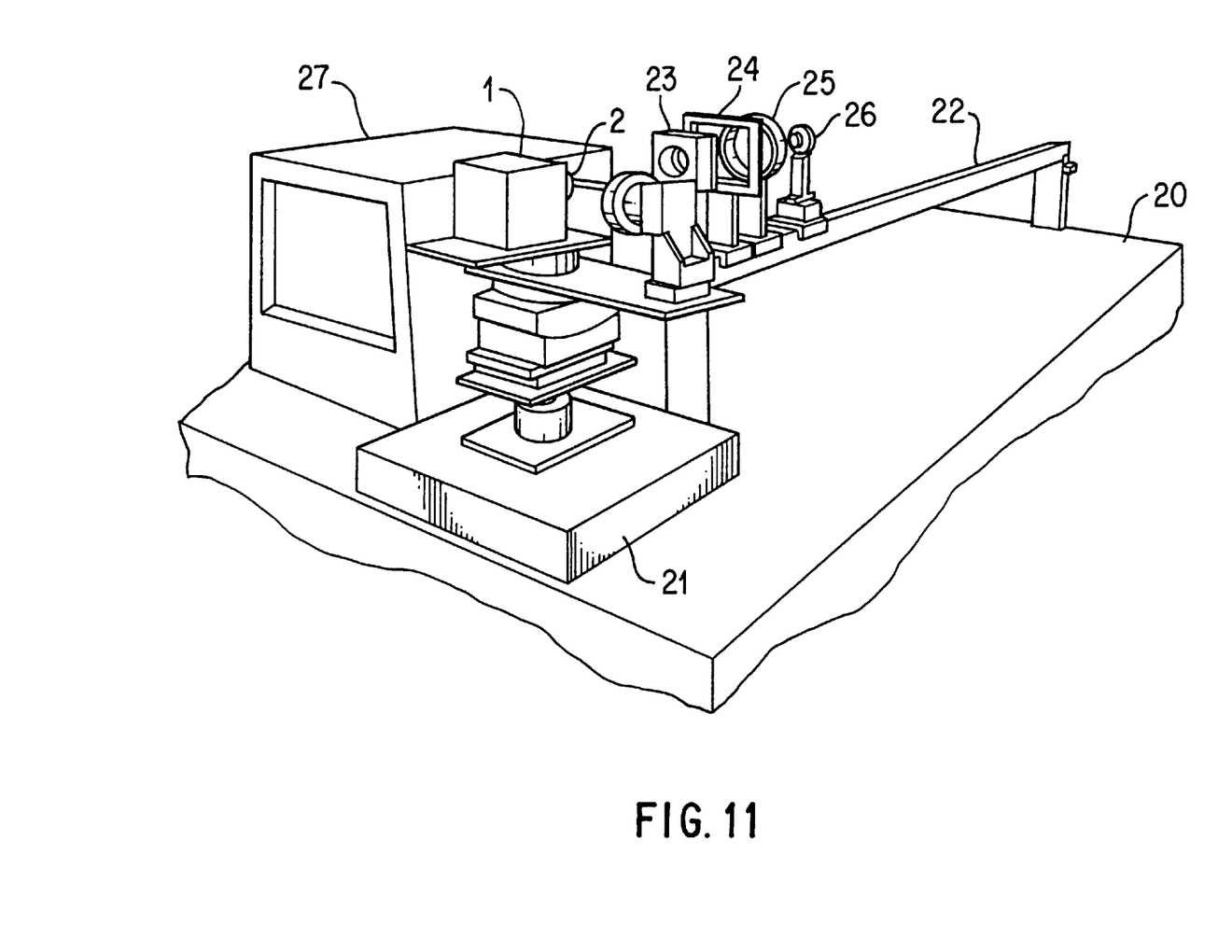
FIG. 11 is a perspective view showing a structure of a system for evaluating the performance of an eyeglass lens by observing a standard measuring object (e.g., chart) at a distance and close-up by using the artificial vision system according to the present invention as shown in FIG. 1.

While it is possible to change the distance between the standard measuring object (e.g., chart) and the eyeglass lens 2 by moving in the X-axis direction by means of the XY stage 14 described in FIG. 1, the movement achieved by the XY stage 14 alone is limited, and the distance cannot be changed arbitrarily from a standard measuring object at a distance to one that is near. Therefore in accordance with another embodiment of the present invention, the standard measuring object is arranged to move in the X-axis direction to permit changing the distance between the eyeglass lens 2 and the standard measuring object in the X-axis direction. FIG. 11 shows a system for observing a standard measuring object (e.g., chart) at a distance or nearby to evaluate the performance of the eyeglass lens 2 (evaluation by the chart) by using the above-mentioned artificial vision system shown in FIG. 1.

As shown in FIG. 11, the artificial vision system in FIG. 1 is set on a mount 21 on a base 20. An X rail 22 is disposed on the base 20 along the X-axis direction which is the direction of the optical axis (visual axis) of the artificial vision camera 1. The chart, an illuminating optical system for illuminating the chart, etc., are set on the X rail 22. Specifically, disposed on the X rail 22 are a collimator box 23 to which the chart is attached, a diffusing plate 24, a collimator lens 25, an illuminator 26, etc. Further, a monitor 27 for displaying an image of the chart shot by the artificial vision camera 1 is provided on the base 20. There is also provided a personal computer (not shown) for an automatic stage control for controlling the turning and parallel movement of the rotary stage 7, the XY stage 14, etc., of the artificial vision system and for outputting images to the monitor 27.

Figure 12:
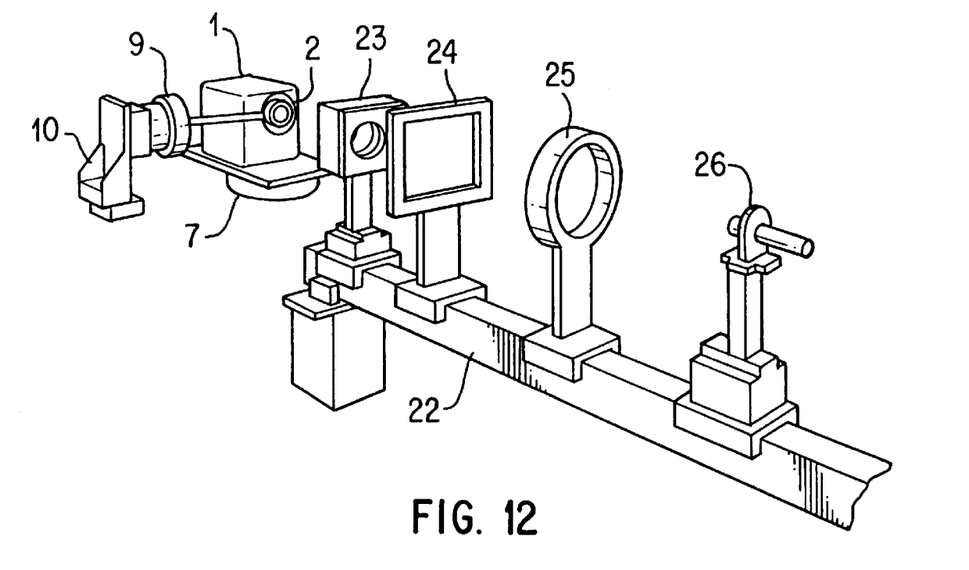
FIG. 12 is a perspective view showing a schematic arrangement for measuring far-sightedness by using the system in FIG. 11.

Next, an example of measuring far-sightedness by using the system shown in FIG. 11 will be explained by reference to FIG. 12. As shown in the figure, the collimator box 23, the diffusing plate 24, the collimator lens 25 and the illuminator 26 are arranged in order from a side nearest the artificial vision camera 1 on the X rail 22. Three dimensional parallel movement and turning is applied to the eyeglass lens 2 and the artificial vision camera 1 by the above-mentioned turning and parallel movement mechanism to control the direction of the optical axis (visual axis) of the artificial vision camera 1 through the eyeglass lens 2 so that the camera 1 always points to the chart. Light from the illuminator 26 is collimated by the collimator lens 25 and is then irradiated to the diffusing plate 24. The illumination light which has become homogeneous by having been diffused by the diffusing plate 24 is illuminated to the chart on the collimator box 23 and light (an image) which is transmitted through the chart is collimated by a collimator lens of the collimator box 23 to be input to the artificial vision camera 1.

Figure 13:
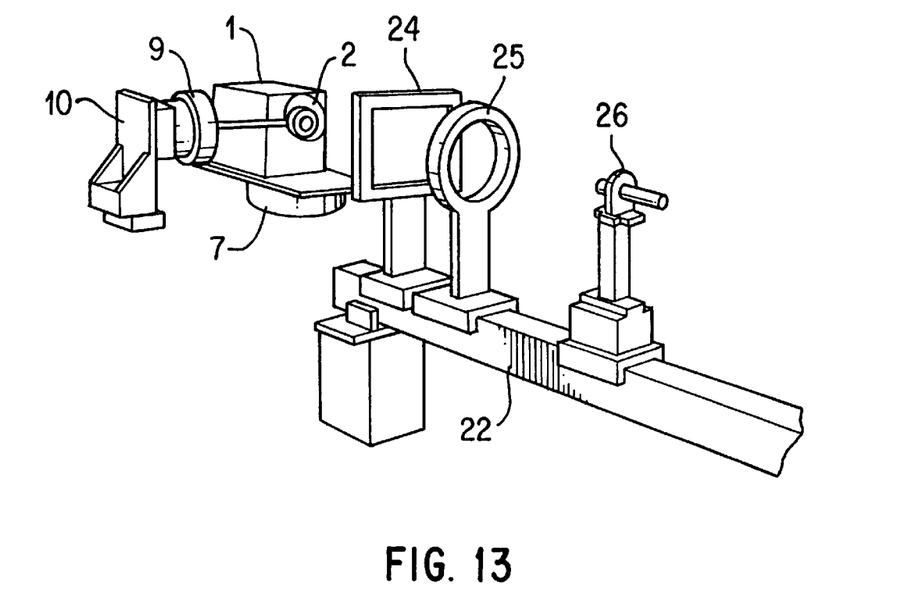
FIG. 13 is a perspective view showing a schematic arrangement for measuring near-sightedness by using the system in FIG. 11.

An example of measuring near-sightedness by using the system shown in FIG. 11 will now be explained by reference to FIG. 13. The diffusing plate 24, the collimator lens 25 and the illuminator 26 are disposed in order from a side nearest the artificial vision camera 1 on the X rail 22. The chart is attached to the diffusing plate 24. Light from the illuminator 26 is collimated by the collimator lens 25 and is irradiated to the diffusing plate 24. The homogeneous illumination light which has been diffused by the diffusing plate 24 is irradiated to the chart attached to the diffusing plate 24 and light (an image) which is transmitted through the chart enters the artificial vision camera 1.

It is also possible, according to the present invention, to arrange the system to view an image through a far-sighted section or a near-sighted section of the eyeglass lens 2 by setting a visual acuity chart in front of the artificial vision camera 1 of the artificial vision system in FIG. 1 without using the system as shown in FIG. 11.

The artificial vision lens system 3 of the present embodiment is adjusted to the optical constants of the paraxial area of Glustrand's precision simulated eye and is not designed by considering image forming characteristics. To the contrary, the image in the simulation of images of a currently developed computer visual system is calculated to be a retinal image of the simulated eye which has passed through the glass lens in the respective sight line directions, and is believed to represent the image forming performance on the retina. On the other hand, the image obtained from the artificial vision system of the present invention is an image taken in a small angle of view (around the fovea of the retina—about 5 degrees) and the image obtained does not represent image forming performance. The evaluation by the observation of the image according to the present system is an utmost relative evaluation.

Although it is not possible to simulate by a computer when the shape of the eyeglass lens is not known in advance, e.g., a eyeglass lens having a manufacturing error, or an eyeglass lens whose design values are unknown, the artificial vision system according to the present invention allows an image to be observed in real-time by adjusting the standard measuring object (e.g., chart) and the optical axis (visual axis) of the artificial vision camera passing through the eyeglass lens.

While progressive multi-focus lenses and the like are eyeglass lenses which take human technological considerations into account in their optical design, there has heretofore been no lens meter or the like for correctly evaluating such lenses. The artificial vision system according to the present invention is particularly useful in evaluating such lenses in conjunction with the retinal image simulation result obtained when evaluated by a computer.

As described above in detail, the artificial vision lens system of the present invention is designed based on optical constants of the paraxial area calculated from a simulated eye, so that the system can fully well approximate the optical characteristics of human eyes in the paraxial area. The system can therefore also be manufactured relatively easily. In addition, the use of the artificial vision lens system according to the present invention allows the retinal image of naked eyes to be simulated.

Furthermore, the artificial vision lens system of the present invention is designed based on the optical constants in the paraxial area calculated from a simulated eye, so that the positional relationship between the eyeglass lens and the position of the object side principal point of the eyeball can be simulated. In this manner, the position of the eyeglass lens with respect to the object side principal point of the artificial vision lens system and the position of the pupil entrance of the artificial vision lens system are correctly set in correspondence to the positional relationship between the eyeglass lens and the eyeball. Also, the brightness of images and the size of the view field do not change and the retinal image when a subject wears an eyeglass lens may be accurately simulated.

Still more, the artificial vision camera according to the present invention allows the retinal image when a subject wears an eyeglass lens to be in real-time.

While the present invention has been described with reference to certain preferred and illustrative embodiments, one of ordinary skill in the art will recognize that additions, deletions, substitutions, modifications and improvements can be made while remaining within the spirit and scope of the present invention as determined solely by the appended claims.

What is claimed is:

1. An artificial vision lens system for simulating an optical system of an eyeball, comprising an artificial vision camera having an arrangement of lenses having optical constants of a paraxial area calculated from a simulated eye.

2. An artificial vision lens system according to claim 1, wherein said simulated eye is a Glustrand's precision simulated eye.

3. The artificial vision lens system according to claim 2, wherein said artificial vision camera has an object side and further comprises, arranged sequentially from the object side of the camera, a front lens group having negative refracting power, a stop, and rear lens group having positive refracting power, wherein a focal position of the camera is controllable by moving the rear lens group.

4. The artificial vision lens system according to claim 2, wherein said artificial vision camera further comprises a planar image-pickup arranged to pickup an image picked up by the camera.

5. The artificial vision lens system according to claim 4, wherein said planar image-pickup comprises a CCD.

6. The artificial vision lens system according to claim 5, further comprising a display operably connected to display an image picked up by the artificial vision camera.

7. The artificial vision lens system according to claim 1, wherein said artificial vision camera has an object side and further comprises, arranged sequentially from the object side of the camera, a front lens group having negative refracting power, a stop, and rear lens group having positive refracting power, wherein a focal position of the camera is controllable by moving the rear lens group.

8. The artificial vision lens system according to claim 1, wherein said artificial vision camera further comprises a planar image-pickup arranged to pickup an image picked up by the camera.

9. The artificial vision lens system according to claim 8, wherein said planar image-pickup comprises a CCD.

10. The artificial vision lens system according to claim 9, further comprising a display operably connected to display an image picked up by the artificial vision camera.

11. An artificial vision lens system for simulating an optical system of an eyeball, comprising an artificial vision camera having optical constants of a paraxial area calculated from a simulated eye, and a holder configured to hold an eyeglass lens, the holder being arranged to simulate relative positions between an eyeglass lens and an object side principal point of an eyeball when a subject wears an eyeglass lens.

12. An artificial vision lens system according to claim 11, wherein said simulated eye is a Glustrand's precision simulated eye.

13. The artificial vision lens system according to claim 11, wherein said artificial vision camera has an object side and further comprises, arranged sequentially from the object side of the camera, a front lens group having negative refracting power, a stop, and rear lens group having positive refracting power, wherein a focal position of the camera is controllable by moving the rear lens group.

14. The artificial vision lens system according to claim 11, wherein said artificial vision camera further comprises a planar image-pickup arranged to pickup an image picked up by the camera.

15. The artificial vision lens system according to claim 14, wherein said planar image-pickup comprises a CCD.

16. The artificial vision lens system according to claim 15, further comprising a display operably connected to display an image picked up by the artificial vision camera.

17. A method for simulating optics of an eyeball, comprising the steps of:

providing an artificial vision camera having optical constants of a paraxial area calculated from a simulated eye;

disposing an eyeglass lens relative to the artificial vision camera in a position simulating the relative position of an eyeglass lens and an object side principal point of an eyeball of a subject wearing the eyeglass lens.

18. A method according to claim 17, wherein said simulated eye is a Glustrand's precision simulated eye.

19. A method according to claim 18, wherein the artificial vision camera has an object side and comprises, arranged sequentially from the object side of the camera, a front lens group having negative refracting power, a stop, and rear lens group having positive refracting power, wherein a focal position of the camera is controllable by moving the rear lens group.

20. A method according to claim 19, wherein said artificial vision camera comprises a planar image-pickup arranged to pickup an image picked up by the camera.

* * * * *